US005981186A

United States Patent [19]
Gabe et al.

[11] Patent Number: 5,981,186
[45] Date of Patent: Nov. 9, 1999

[54] METHOD AND APPARATUS FOR DNA-SEQUENCING USING REDUCED NUMBER OF SEQUENCING MIXTURES

[75] Inventors: Chris Gabe, Toronto; Rodney D. Gilchrist, Oakville, both of Canada

[73] Assignee: Visible Genetics, Inc., Toronto, Canada

[21] Appl. No.: 08/892,003

[22] Filed: Jul. 14, 1997

Related U.S. Application Data

[63] Continuation-in-part of application No. 08/497,202, Jun. 30, 1995, Pat. No. 5,853,979, application No. 08/577,858, Dec. 22, 1995, Pat. No. 5,834,189, application No. 08/670,534, Jun. 27, 1996, Pat. No. 5,916,747, and application No. PCT/US96/20202, Dec. 19, 1996.

[51] Int. Cl.$^6$ .............................. C12Q 1/68; C12P 19/34
[52] U.S. Cl. ................................ 435/6; 435/91.1; 422/50; 422/68.1; 422/101
[58] Field of Search ........................ 435/6, 91.1; 422/50, 422/68.1, 101

[56] References Cited

U.S. PATENT DOCUMENTS

| | | | |
|---|---|---|---|
| 3,742,202 | 6/1973 | Spreitzhofer | 235/183 |
| 4,329,591 | 5/1982 | Fujiwara et al. | 250/548 |
| 4,720,786 | 1/1988 | Hara | 364/413 |

(List continued on next page.)

FOREIGN PATENT DOCUMENTS

| | | |
|---|---|---|
| 0592060 | 4/1994 | European Pat. Off. .......... C12Q 1/68 |
| 4405251 | 8/1994 | Germany . |
| 2225139 | 5/1990 | United Kingdom . |

OTHER PUBLICATIONS

Bowling et al., "Neighboring Nucleotide Interactions During DNA Sequencing Electrophoresis", *Nucleic Acids Res.* 19: 3089–3097 (1991).

Giddings et al., "An Adaptive, Object Oriented Strategy for Base calling in DNA Sequences", *Nucleic Acids Res.* 21: 4530–4540 (1993).

Golden II, et al., "Pattern Recognition for Automated DNA Sequencing: I. On–Line Signal Conditioning and Feature Extraction for Basecalling".

Tibbetts et al., "Neural Networks for Automated Basecalling of gel–based Sequencing Ladders".

Smith et al., "Fluorescence detection of automated DNA sequence analysis", *Nature* 321: 674–679 (1986).

Mayrand et al., "The use of fluorescence detection and internal lane standards to size PCR products".

(List continued on next page.)

*Primary Examiner*—Kenneth R. Horlick
*Attorney, Agent, or Firm*—Oppedahl & Larson LLP

[57] ABSTRACT

The sequence of a target nucleic acid polymer can be determined by (a) performing a first chain-extension sequencing reaction on the target nucleic acid polymer in a reaction mixture containing first and second chain-terminators to produce a first product mixture containing commonly-labeled polynucleotide fragments complementary to a first strand of the target nucleic acid polymer, each fragment in the mixture being terminated with the first or second chain-terminator; (b) performing a second chain extension sequencing reaction on the target nucleic acid polymer in a reaction mixture containing the first and a third chain-terminator to produce a second product mixture containing commonly-labeled polynucleotide fragments complementary to the first strand of the target nucleic acid polymer, each fragment in the mixture being terminated with the first or the third chain-terminator, said first, second and third chain-terminators each being different; and (c) evaluating the lengths of the polynucleotide fragments in the first and second product mixtures to determine the sequence of the target nucleic acid polymer. In the evaluation step, the first and second product mixtures can be evaluated in two separate lanes of a gel, in which case the labels employed in the two chain extension sequencing reactions can be the same. Alternatively, if the labels employed in the two chain extension reactions are different and spectroscopically distinguishable from one another, the first and second product mixtures can be combined before electrophoresis and the entire analysis can be performed in a single lane of a gel.

25 Claims, 7 Drawing Sheets

U.S. PATENT DOCUMENTS

| | | |
|---|---|---|
| 4,811,218 | 3/1989 | Hunkapiller et al. ............... 364/413.01 |
| 4,823,007 | 4/1989 | Hanson ................................ 250/327.2 |
| 4,865,968 | 9/1989 | Orgel et al. ................................ 435/6 |
| 4,941,092 | 7/1990 | Hara et al. ......................... 364/413.15 |
| 4,960,999 | 10/1990 | McKean et al. ...................... 250/461.1 |
| 4,982,326 | 1/1991 | Kaneko ............................... 364/413.01 |
| 5,108,179 | 4/1992 | Myers ...................................... 356/344 |
| 5,119,316 | 6/1992 | Dam et al. .............................. 364/498 |
| 5,124,247 | 6/1992 | Ansorge ..................................... 435/6 |
| 5,190,632 | 3/1993 | Fujimiya et al. ................... 204/299 R |
| 5,213,673 | 5/1993 | Fujimiya et al. ................... 204/299 R |
| 5,246,866 | 9/1993 | Nasu et al. ................................ 436/94 |
| 5,273,632 | 12/1993 | Stockham et al. ................... 204/180.1 |
| 5,290,419 | 3/1994 | Kambara et al. .................... 204/299 R |
| 5,360,523 | 11/1994 | Middendorf et al. ................ 204/182.8 |
| 5,365,455 | 11/1994 | Tibbetts et al. ......................... 364/497 |
| 5,419,825 | 5/1995 | Fujii ......................................... 204/299 |
| 5,502,773 | 3/1996 | Tibbets et al. ........................... 382/192 |
| 5,667,971 | 9/1997 | Hochberg ..................................... 435/6 |

OTHER PUBLICATIONS

Koutny et al., "Automated Image Analysis fir Distortion Compensation in Sequencing Gel Electrophoresis" *Applied Spectroscopy* 46: 136–141 (1992).

Ingber and Rosen, "Genetic Algorithms and Very Fast Simulated Annealing: A Comparison" *Mathematics and Computer Modelling* 16: 87–100 (1992).

Ingber, L., "Simulated Annealing: Practice versus Theory", *Mathematical and Computer Modelling* 18: 29–57 (1993).

Ingber,L., "Adaptive Simulated Annealing (ASA) : Lessons Learned". *Control and Cybernetics* 1995).

Ingber, L., "Very Fast Simulated Re–Annealing" *Mathematical and Computer Modelling* 12: 967–973 (1989).

Landegren et al., "DNA Diagnostics—Molecular Techqnies and Automation" *Science* 242: 229–237 (1988).

Sarkar et al., "Dideoxy Fingerprinting (ddF) : A Rapid and Efficient Screen for the Presence of Mutations" *Genomics* 13: 441–443 (1992).

Lin et al., "Characterization of Genetic Defects of Hemophilia A in Patients of Chinese Origin" *Genomics* 18: 496–504 (1993).

Langemeir et al, "Application of Cycle Dideoxy Fingerprinting to Screening Heterogenous Populations of the Equine Infectious Anemia Virus", *BioiTechniques* 17: 484–490 (1994).

Krishnamani et al., "Detection of a Novel Arginine Vasopressin Defect by Dideoxy Fingerprinting" *J. Clin. Endocrinol. & Metabol.* 77: 596–598 (1993).

Ellison et al., "Detection of Mutations and Polymorphisms Using Fluorescence–Based Dideoxy Fingerprinting (F–ddF)", *BioTechniques* 17: 742–753 (1994).

Olesen et al., "Chemiluminescent DNA Sequencing with Multiplex Labeling", *Biotechniques* 15: 480–485 (1993).

Kambara et al., "Real Time Automated Simultaneous Double Stranded DNA Sequencing Using Two–Color Fluorophore Labelling" *Biotechnology* 9: 63–66 (1991).

CONDITIONED DATA TRACE

FIG. 4A

RAW DATA

SMOOTHED PEAKS

AND

RAW DATA

FIG. 5B

SMOOTHED PEAKS

FIG. 5C

AND

METHOD AND APPARATUS FOR DNA-SEQUENCING USING REDUCED NUMBER OF SEQUENCING MIXTURES

This application is a continuation-in-part of U.S. patent applications Ser. No. 08/497,202 filed Jun. 30, 1995, U.S. Pat. No. 5,853,979, Ser. No. 08/577,858 filed Dec. 22, 1995, U.S. Pat. No. 5,834,189, and Ser. No. 08/670,534 filed Jun. 27, 1996, now U.S. Pat. No. 5,916,747, and of PCT Patent Application No. PCT/US96/20202 filed Dec. 19, 1996 designating the United States, all of which are incorporated herein by reference.

BACKGROUND OF THE INVENTION

This application relates to an improved method and apparatus for determining the sequence of nucleic acid polymers, e.g., DNA.

Nucleic acid sequencing is conventionally performed using one of two approaches: the chain extension reaction disclosed by Sanger et al., *Proc. Nat'l Acad. Sci. (USA)* 74: 5463–5467 (1977); and chain degradation sequencing disclosed by Maxam & Gilbert, *Proc. Nat'l. Acad. Sci. (USA)* 74: 560–564 (1977). Chain extension sequencing, which is the more extensively used of the two approaches, utilizes a primer and a template-dependent polymerase enzyme which extends template-hybridized primer to produce polynucleotide fragments. Chain-terminating nucleotide analogs, such as dideoxynucleotide triphosphates, are included in the reaction, and these chain terminators, when incorporated, prevent further extension of the primer by the polymerase enzyme. As a result, a chain termination reaction containing, e.g, dideoxyadenosine triphosphate (ddATP) produces a mixture of polynucleotide fragments of differing lengths, each fragment ending in ddA. Other chain terminators produce fragments mixtures ending in other nucleotides. Performing one reaction with a terminator corresponding to each base (A, C, G and T), and evaluating the sizes of the fragments permits determination of the sequence of the original template polymer.

Automated apparatus for performing chain extension sequencing is available commercially. For example, single-dye automated sequencers such as the ALF-Express (Pharmacia LKB, Piscataway N.J.) usually run one separate reaction per lane. Methods to increase throughput in such automated DNA sequencers are currently constrained by the fact that in order to obtain a DNA sequence, four channels of data are required, one for each of the nucleotide bases A, C, G or T. Multi-dye sequencers such as the Prism 377 (Applied Biosystems Inc., Foster City Calif.) allow 4 reactions to be run in one lane. This method improves the throughput of a single gel 4-fold but still requires four channels of data per DNA sequence.

Intensity labeling has been proposed as a method for sequencing DNA in a single channel. In these methods, the ladder of all four sequencing reaction products (A, C, G, or T) is run in a single lane, and the species are distinguished by the amount of detected reaction product. For instance, U.S. Pat. Nos. 4,962,020, 5,122,345 and 5,409,881, illustrate a chain extension sequencing chromatogram where the relative amounts of the chain-terminators and thus the relative intensities of the reaction products are G>A>T>C. Ansorge et al (1990) "One label, one tube, Sanger DNA sequencing in one and two lanes on a gel", *Nuc. Acid. Res.* 18: 3419–20 illustrates a chain termination method where the relative amounts of the chain terminators are T>C>G>A. A two-lane intensity labeling method is disclosed in U.S. Pat. No. 5,124,247 issued to Ansorge. Negri et al. (1991) A Single-Reaction Method for DNA Sequence Determination. *Anal. Biochem.* 197:389–395 discloses a chain degradation method of intensity labeling where A=G>C (and T is not analyzed). None of these methods have been employed commercially, perhaps because the intensity of labeling of reaction products changes substantially during the course of a single analysis.

An alternative method that does not depend on intensity labeling to increase throughput takes advantage of the fact that, at least in the diagnostic setting, the DNA sequence of a diagnostic gene is already known. In this case, the method determines which sequence the patient sample matches from a library of known sequence variants. This frequently can be done on the basis of a single nucleotide chain termination reaction as disclosed in U.S. patent application Ser. Nos. 08/497,202 and 08/577,858, assigned to the assignee of the instant invention. Single nucleotide sequencing may mean testing a known gene, such as an oncogene, for mutations such as nucleotide insertions, deletions, inversions or substitutions. It may mean testing a known polymorphic locus to identify which allelic variant(s) are present. It may mean testing a patient sample for the presence of a known pathogen, or testing for a known variation of a known pathogen. In each of these cases, at least some patient samples can be identified with certainty by determining the positions of less than all 4 nucleotides, hence using less than 4 channels.

Reduction the number of data channels required can also be obtained by applying algebraic coding methods from information theory. A method for DNA sequence analysis that resembles data compression techniques used in telecommunications was disclosed by Nelson et al. (1993) "Sequencing Two DNA Templates In Five Channels By Digital Compression" *Proc. Nat'l Acad. Sci. (USA)* 90:1647–1651. This paper describes how sequences of one DNA template can be determined in three channels; and how two DNA templates can be determined simultaneously using five channels. The paper does not teach how to reduce the number of channels for a full DNA sequence below these amounts.

It is an object of the instant invention to provide a method of increasing the throughput of an electrophoretic gel by reducing the number of channels necessary to identify the sequence of a DNA fragment.

It is a further object of the instant invention to provide a method of increasing the throughput of an electrophoretic gel that does not require spectrally distinguishable fluorophores or intensity labeling.

It is a further object of the invention to simplify the number of steps required to identify the sequence of a DNA fragment.

It is an object of the present invention to provide a diagnostic method and apparatus which identifies a DNA sequence in a patient but does not require the explicit identification of location of all 4 nucleotides of the DNA sequence.

SUMMARY OF THE INVENTION

In accordance with the invention, these and other objects are achieved using a method for identifying the sequence of a target nucleic acid polymer comprising the steps of:

(a) performing a first chain-extension sequencing reaction on the target nucleic acid polymer in a reaction mixture containing first and second chain-terminators to produce a first product mixture containing commonly-labeled polynucleotide fragments complementary to a first strand of the target nucleic acid polymer, each fragment in the mixture being terminated with the first or second chain-terminator;

(b) performing a second chain extension sequencing reaction on the target nucleic acid polymer in a reaction mixture containing the first and a third chain-terminator to produce a second product mixture containing commonly-labeled polynucleotide fragments complementary to the first strand of the target nucleic acid polymer, each fragment in the mixture being terminated with the first or the third chain-terminator, said first, second and third chain-terminators each being different; and (c) evaluating the lengths of the polynucleotide fragments in the first and second product mixtures to determine the sequence of the target nucleic acid polymer. In the evaluation step, the first and second product mixtures can be evaluated in two separate lanes of a gel, in which case the labels employed in the two chain extension sequencing reactions can be the same. Alternatively, if the labels employed in the two chain extension reactions are different and spectroscopically distinguishable from one another, the first and second product mixtures can be combined before electrophoresis and the entire analysis can be performed in a single lane of a gel.

The method of the invention can be performed using a sequencing apparatus which has data processing capability for determining the sequence of the target nucleic acid from only two data channels. One data channel reflects peak positions for fragments ending with the first and second chain-terminators and one data channel reflects peak positions for fragments ending with the first and third chain-terminators.

DETAILED DESCRIPTION OF THE INVENTION

The present invention provides a method and apparatus of sequencing of a target nucleic acid polymer. In the method of the invention, two chain-extension sequencing reactions are performed on the target nucleic acid polymer to produce two product mixtures.

As used in the specification and claims hereof, the term "chain-extension sequencing reaction" refers to any technique for generating polynucleotide fragments by extension of an oligonucleotide primer that is hybridized to the target nucleic acid in the presence of chain-terminators. Examples of such processes include the basic methodology described by Sanger et al.; cycle sequencing as described in U.S. Pat. No. 5,547,859; coupled amplification and sequencing (CAS) as described in U.S. Pat. No. 5,427,911, or the single-tube sequencing method described in U.S. patent application Ser. No. 08/684,498, filed Jul. 19, 1996 U.S. Pat. No. 5,830,657 and the PCT Application No. PCT/US97/07135, filed Apr. 29, 1997 all of which are incorporated herein by reference.

As discussed above, such chain-extension sequencing reactions incorporate chain-terminating analogs of the conventional nucleotides A, C, G and T. These chain terminating analogs are referred to in the specification and claims of this application as "chain terminators." Examples of chain terminators include dideoxynucleotide triphosphates and arabinonucleotide triphosphates (U.S. Pat. No. 5,547,859).

In accordance with the invention, a first termination reaction is performed which generates fragments terminated at two of the four standard nucleotides by having two types of chain terminators present in the reaction. A second termination reaction is performed which also generates fragments terminating at two of the four standard nucleotides using two type of chain terminators, one of which is also used in the first reaction and the other of which is not. The two reactions preferably use the same primer or primers, but can use different primers as long as the reaction products formed in the two reactions start at the same location. The reaction products of each reaction are separated on a length basis, generally by electrophoresis, detected and reported in a chromatogram format containing two data channels, one for each reaction mixture.

Figure 1:
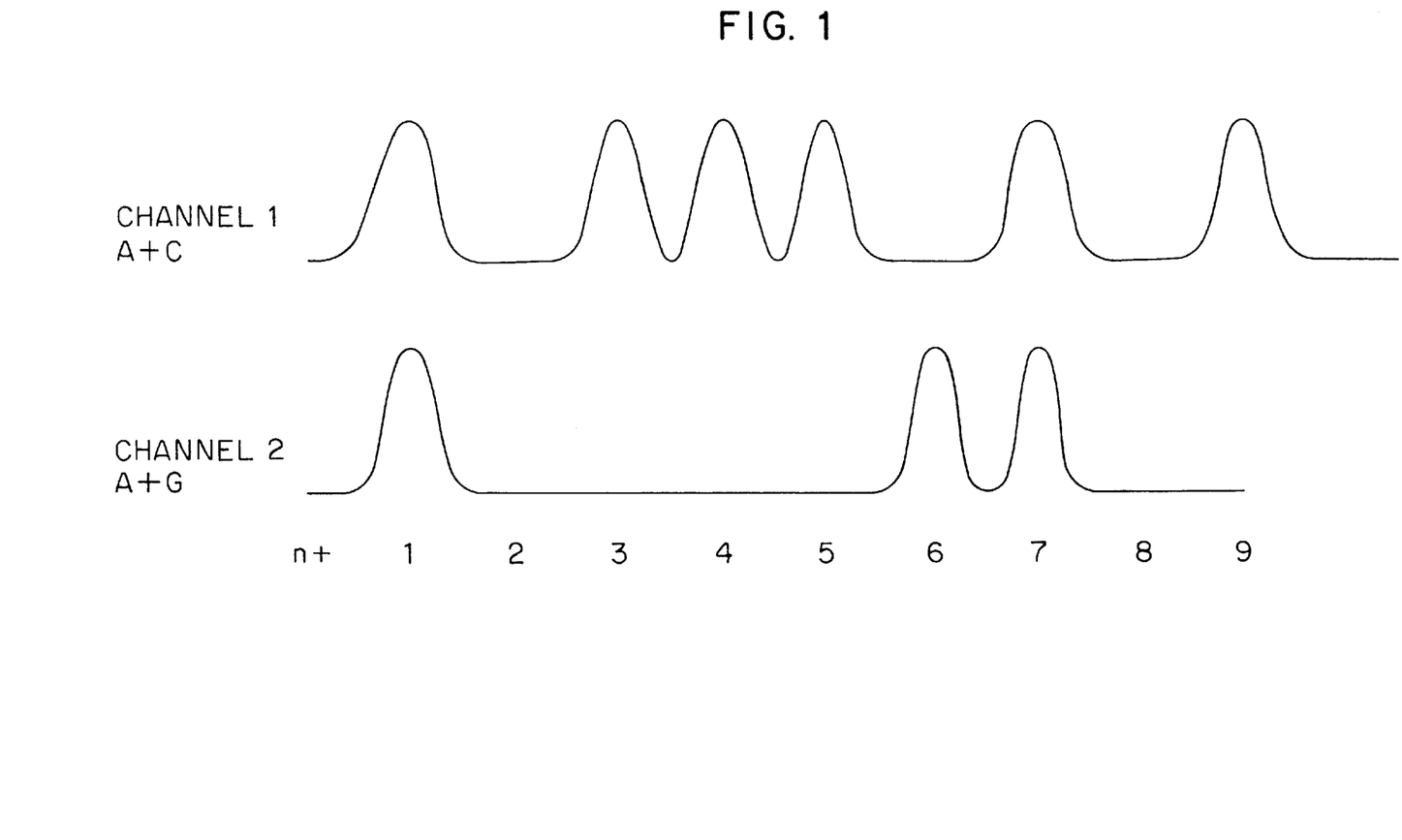
FIG. 1 shows a hypothetical data set of two data channels for sequencing a 9 nt target nucleic acid polymer using the method of the invention.

FIG. 1 illustrates a hypothetical pair of data channels obtained for sequencing of a target nucleic acid polymer having the sequence ATACCGATC. As will be apparent to persons skilled in the art, this exemplary sequence is shorter than a real sequence, and is provided only for ease of explanation. FIG. 1 assumes that the first reaction mixture used in generating these traces contained ddATP and ddCTP as chain terminators, and the second reaction mixture contained ddATP and ddGTP.

Data analysis is based on a comparison of peaks present in the two data channels. When a peak is present in both data channels, as for the peak at position 1, the peak is assigned as an A because ddATP was present in both reaction mixtures. When a peak is present in neither data channel, as is the case at position 2, the peak is assigned as a T because ddTTP was not included in either reaction mixture. When a peak is present only in data channel 2, as is the case for the peak at position 6, the peak is assigned as G because reaction mixture 2 contained ddGTP, but reaction mixture 1 did not. Finally, when a peak is present only in data channel 1, as is the case for the peak at position 3, the peak is assigned as C because reaction mixture 1 contained ddCTP, but reaction mixture 2 did not.

Of course, real data does not present as neat a picture as that set forth in the hypothetical results shown in FIG. 1. The heights of the peaks may be variable, and the quite frequently the spacing between adjacent peaks will be variable. This means that additional treatment of the data may be necessary to obtain a meaningful result for real sequencing data. On the other hand, as discussed below, the idiosyncracies of real data can actually facilitate the analysis of the data obtained using the method of the invention.

The data traces obtained according to the method of the invention may be analyzed using various approaches to compensate for real world variability. The basic analysis of the data traces obtained in the two reactions requires the correct alignment of the two traces and identification of peaks and gaps.

Unlike the case of four-lane DNA sequencing with single-base traces, where alignment is frequently a challenge, the data traces of the present invention are frequently automatically aligned such that no additional alignment is necessary. Thus, for example, if the two traces come from different dyes in a single lane of a sequencing device, the positional equivalency is guaranteed. Comparable automatic alignment can also occur for some instruments which produce very consistent separations. When alignment is necessary, however, it can be done in any of several ways.

First, we have observed that it is surprisingly easy to align the two data traces obtained using the invention by visual inspection. This is so because roughly half of the peaks in each lane are in common. With perfect peaks they would be indistinguishable so you couldn't align, but in general the peaks obtained are far from perfect. There are many idiosyncracies, some quite significant in size and shape. It turns out most of those idiosyncracies come from the bases—they are not just random noise or single-occurrence fluctuations in each lane. So, about half of the idiosyncracies are in common to the two lanes. A lot of those happen where the other bases are relatively quiescent, so you can see them clearly. The result is that the location where one lane overlays another is readily apparent on visual inspection. Thus, in one embodiment of the invention, an operator can electronically "slide" the traces with respect to each other to achieve correct alignment.

Initial alignment of the data traces can also be automated. For many clinical and diagnostic applications where the putative sequence is known, this can be accomplished by a signal-based comparison of the two data traces with a standard data trace for the known sequence in the manner disclosed in parent application Ser. No. 08/497,202. Each data trace is first independently aligned to a standard data trace by determining a set of "normalization coefficients" which reflect the displacement, stretching or shifting of the data trace, or of segment thereof, which are necessary to obtain a suitably high degree of correlation between the experimental and standard data traces. The normalization coefficients are then applied to the experimental data traces to produce normalized data traces. These normalized data traces align the experimental data traces indirectly by aligning them to the standards.

Alignment by comparison to a known sequence can also be performed after peak identification using a text-based, rather than a signal-based process, and this process is much faster than a signal-based process. In this process, peaks are first identified, using for example the techniques described in this application or in U.S. patent application Ser. No. 08/577,858 and PCT Application No. PCT/US96/20202 which are incorporated herein by reference. The identified peaks are then used to construct a two-letter (the letters indicating peak or not peak) text file for each data trace. Alignment of the text files is then performed by comparing these experimental text files to two standard text files which are two-letter base lists for the known sequence. Algorithms for performing this comparison are well known in the art, for example Smith and Waterman's local homology algorithm (*J. Mol. Biol.* 147: 195–197 (1981)) and Needleman and Wunch's global alignment technique (*J. Mol. Biol.* 48: 443–453 (1970)), and are implemented in the GeneLibrarian™ software available from Visible Genetics Inc. Both signal-based and text-based approaches may reveal areas where the alignment does not correspond well. In those regions, the alignment can be interpolated from the nearest regions which do align well.

Automated alignment can also be accomplished by evaluating the data traces for similarities, including reproduced artefacts. To do this, each data traces is reviewed and instances of variations in peak height, compressions, hard stops and other chemistry-induced noise are identified. Common artefacts which appear in both traces are then used as the basis for alignment of the traces.

Once the data traces are aligned correctly the next step is the identification of peaks and of the number of "missing peaks" in each gap in the data. Peaks (or function maxima) can be identified by any method, such as a standard "3 point" method or more sophisticated second order derivative analysis (see U.S. Pat. No. 5,365,455 to Tibbetts et al.) Peaks below a minimum height are deleted on a user defined basis to reduce noise. The peaks detected may represent singletons or multiple peaks or combinations of different shaped peaks. These peaks all need to be deconvolved to provide useable information. Of course, any mistake in determining the number of peaks can result in profound consequences for the patient, so a high standard of accuracy is required.

One approach to facilitate the identification of each peak correctly is to run the products of a parallel sequencing reaction mixture for a standard oligonucleotide (e.g., poly-dA) which will produce peaks at each of the base positions. This approach is fairly straightforward, but it involves an increase in the amount of chemistry which must be performed, and adds an additional lane to the analysis, thereby negating some of the throughput improvement gained using the method of the invention. Thus, it is preferred to use a method for identifying individual peaks which does not require the performance of additional reactions beyond those for making sequencing fragments from the target sequence.

A suitable approach for the identification of peak locations is disclosed in U.S. patent application Ser. No. 08/670, 534. This method employ a gaussian deconvolution whereby a peak is deconvolved into one or more standard gaussian peaks representing singleton peaks. It is found that peaks generated from DNA sequencing reactions using T7 polymerase (Pharmacia, Sweden) and Thermo Sequenase™ (Amersham Life Sciences) generate the most consistent gaussian peaks.

Figure 2:
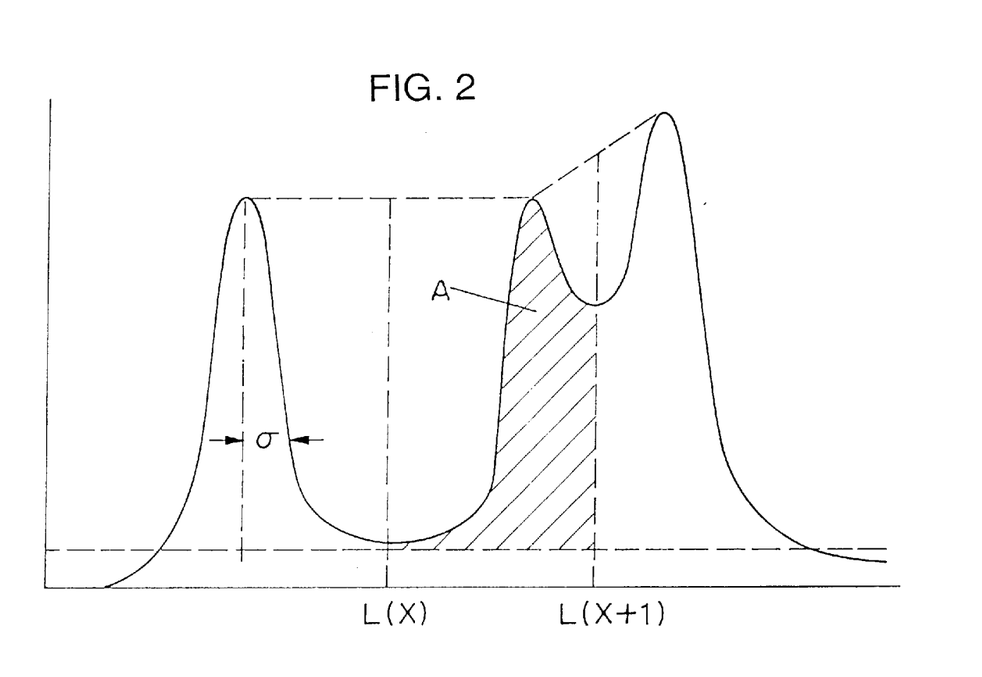
FIG. 2 illustrates a method for determining a standard gaussian peak width.

The standard gaussian peak is determined as shown in FIG. 2. Peaks are located in a data trace from one channel. A line is drawn between peak points. The point on the line halfway between peaks is joined to the data trace by a line L perpendicular to the baseline. The area under the curve A and between the two perpendicular lines (L(x), L(x+1)) is determined. Height (h) is measured from the baseline to the peak. h and A are used to calculate sigma ($\sigma$) according to the equation:

$$\sigma = \frac{A}{h\sqrt{\pi}}$$

where $\sigma$ represents the distance on the x-axis between the peak and the point at which the value of the gaussian function $$y = e^{-(x/\sigma)^2}$$

equals $1/e$.

For each detected peak, $\sigma$ is determined. For those peaks where the length of both L(x) and L(x+1) are greater than ½ h, a linear regression is performed on the value of $\sigma$.

Figure 3:
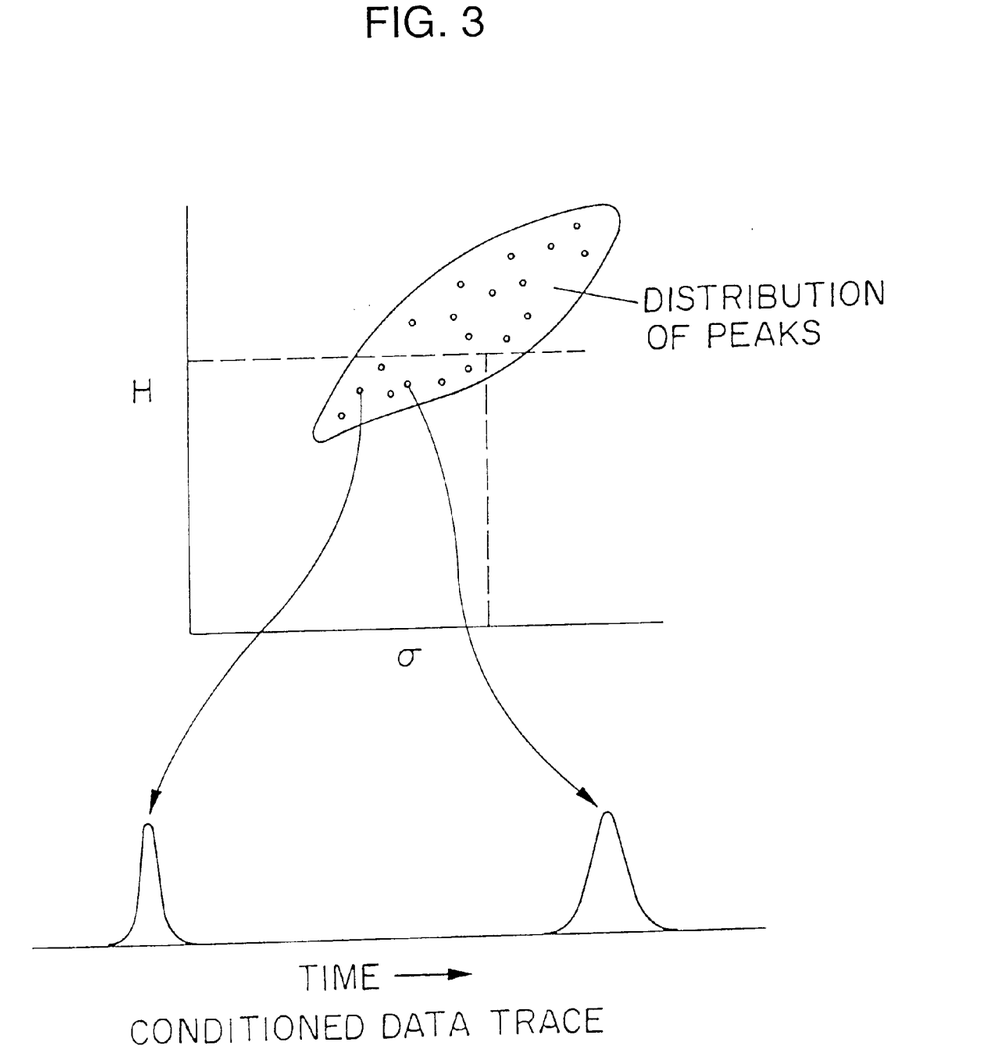
FIG. 3 shows an example of the classification of singletons using the features of peaks in the detected signal.

Statistically, at most about 46% of peaks are expected to represent doubletons, triples or greater, so using the linear regression to correct for a width trend over each window, the narrowest 45% of the peaks are selected for use in constructing a piecewise cubic "singleton width discriminant function" that specifies the width of a singleton at each location in the data array. All peaks in the window that are narrower or equal to this function are deemed to be singletons to a first approximation. This approximation may be further refined using constraints such as peak area, etc. (FIG. 3) In this way, a standard or model singleton gaussian peak height and width at any point on the data trace may be defined.

The characteristics of the standard gaussian peak(s) and the positions of the singletons found via the discriminant function in conjunction with the base width function are then used to classify all the peaks in the aligned data traces. The features (e.g., height, width and/or area) of the standard peak are compared to the features of a detected signal peak to determine the number of bases represented.

Figure 7:
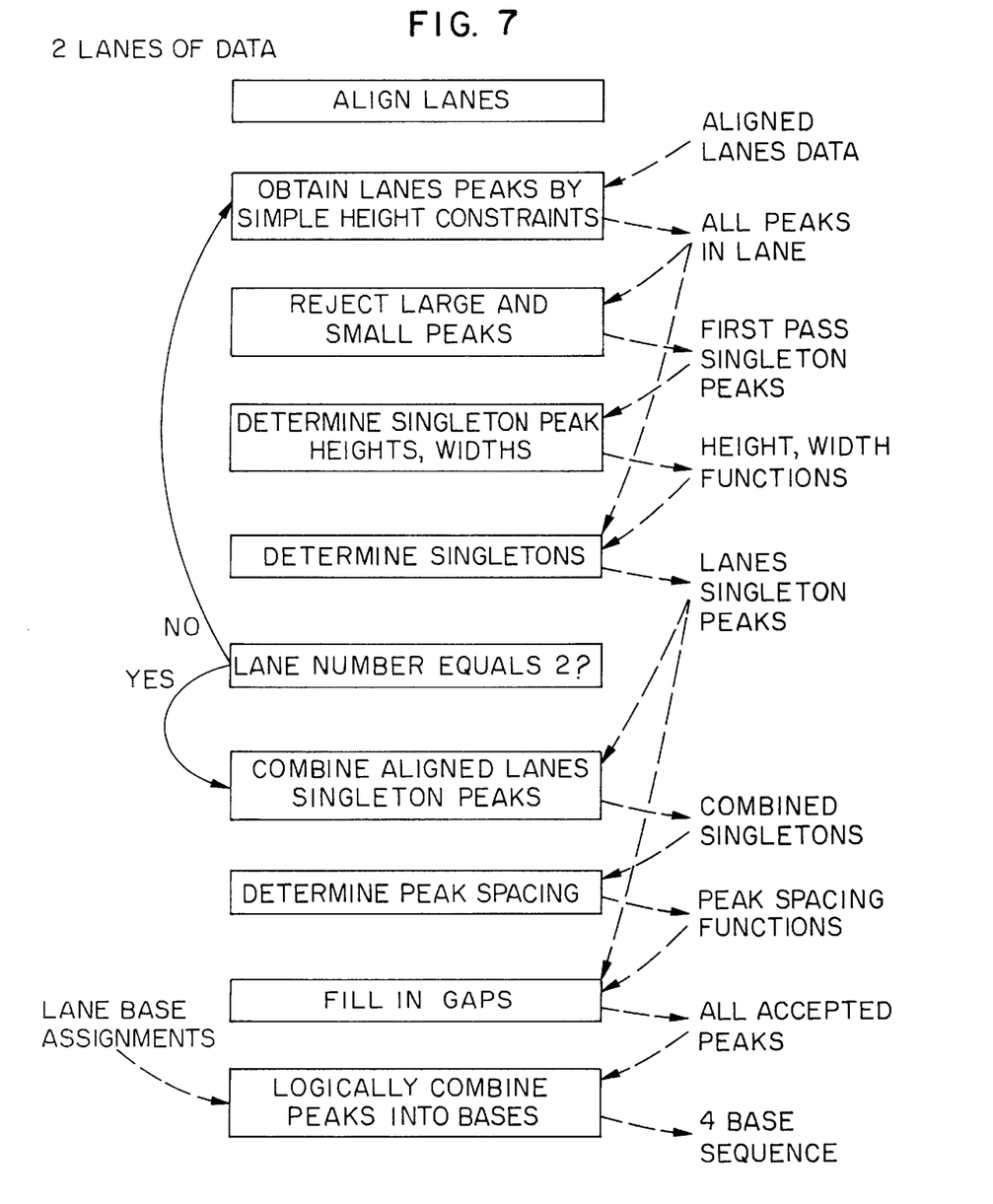
FIG. 7 shows a flow chart for a programmed instruction set useful in the apparatus of the invention.

The identification of peaks can also be carried out in an iterative process as illustrated in FIG. 7. In this process, data from each lane is analyzed to identify peaks based initially on height constraints, with any maximum in a data trace over a defined threshold being considered a peak. The peaks identified in this way are then evaluated based on additional parameters which may include peak height, peak width and peak shape (e.g. symmetry) to identify those "singleton" peaks which are most likely to reflect one and only one base. This subset of the peaks, generally 40 to 50% of the total number of peaks, is then used to define a set of standard singleton height and width functions for the data traces, and these functions are used to reevaluate the data to identify singleton peaks for each lane. In practice, this can be accomplished by identifying the width ($\sigma$) of the $45^{th}$ percentile peak and then selecting those peaks with a width that falls within a threshold percentage of this value. The specific threshold value depends on the experimental apparatus.

The identified singletons are then combined and aligned and used for determination of a standard peak spacing function. The standard peak spacing function can be used to assign non-singleton peaks (which may represent one or more bases due to compressions in the data).

In addition to determining the number of nucleotide bases represented by each peak, the number of missing bases in the gaps between peaks must be determined. Identification of the number of missing peaks can be achieved using a calibration run, conducted in parallel with the experimental run, but is preferably done using analysis of only the experimental data. This can be achieved on the basis of the timing track derived from the singleton list obtained above. The spacing of singletons may change during the course of a run, but at any particular region it can be determined according to the spacing function—i.e. by using the spacing between singletons nearest the area. The singleton peaks generally lie an integral multiple of some peak spacing value (expressed in units of data points) away from their nearest neighbors. The distribution of these separations can be plotted as a histogram, and the large majority of these values should appear near these integral multiples of the true peak to peak spacing. The histogram therefore contains sufficient information to estimate the peak to peak spacing for that region. For example, there may be a cluster of spacings around 7 data points, another near 14 and another near 21, indicating that the base separation is 7 data points. If the distribution of points in the histogram is insufficiently clustered to determine the pattern of spacing, a default value from a neighboring region, or a known spacing based on previous runs with the same acquisition parameters can be used.

Once the peak spacing is determined, the gaps between singletons can be filled with the appropriate number of bases. The space between each adjacent singleton is divided by the base separation for that area, and rounded to the nearest integer. If this shows that one or more bases should be inserted, the estimated number are inserted, spaced evenly between the adjacent singletons. At each of these positions, an "implicit" peak is inserted, unless there is a significant amount of signal in either of the lanes (in which case bases for the significant lane(s) is inserted instead). A good heuristic for assigning peaks from a real lane of data is any lane which is half the expected peak height function or greater at that point.

The result is that the gaps between peaks are deconvolved to ascertain the most likely nearest integral number of peaks in the gap. It is found empirically that this method which is employed by GeneObjects™ software obtains an accuracy sufficient for clinical applications. Even when the peak spacing is estimated only from previous, similar runs, the results can be clinically acceptable. For example when only a genotype is required, and occasional (false) insertions or deletions in the genetic sequence are not of interest, this technique works well.

Finally, the combined list of peaks, along with the knowledge of which two bases is in each lane, is used to determine the base sequence. At each peak position, a boolean logic is applied in which the common base is assigned if both lanes have a peak there, the first lanes other base is assigned if only the first lane has a peak, the second lanes other base is assigned if only the second lane contains a peak, and the fourth, unsequenced, base is assigned for implicit peaks.

Figure 4A:
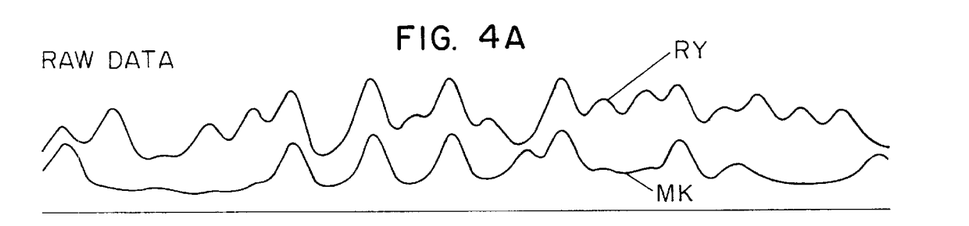
FIGS. 4A–D show data manipulation of real data from sequencing of a target nucleic acid polymer using the method of the invention.
Figure 4B:
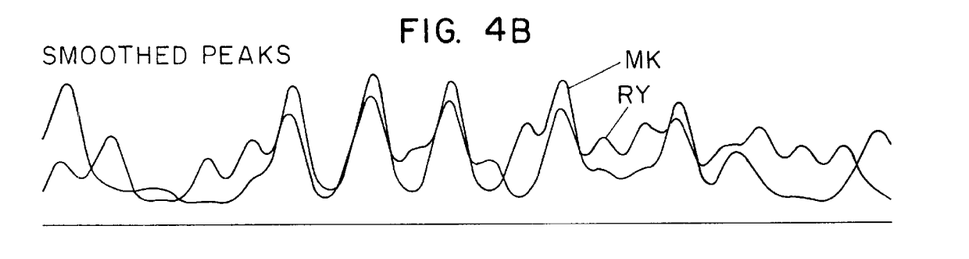

FIGS. 4A–4D illustrate the analysis of aligned data traces obtained using the method of the invention in more detail. FIG. 4A shows raw data for sequencing of a target nucleic acid using the reaction conditions of Example 1. In the chromatogram output of FIG. 4A the data trace designated 21 represents the AC termination reaction products identified from lane 1; while 22 represents the AG reaction products from lane 2. Neither reaction employs a terminator for T. In FIG. 4B the data traces have been smoothed and noise is reduced according to standard signal processing techniques to produce a "conditioned" data trace. Appropriate signal processing techniques which may be used individually or in combination used include background subtraction, low frequency filtration and high frequency filtration.

Background subtraction eliminates the minimum constant noise recorded by the detector. The background is calculated as a measure of the minimum signal obtained over a selected number of data points. This measure differs from low frequency filtration which eliminates low period variations in signal that may result from variable laser intensity, etc.

High frequency filtration eliminates the small variations in signal intensity that occur over highly localized areas of signal. The result after base-line subtraction is a band-pass filter applied to the frequency domain:

$$F(f) = e^{-f^2/\sigma^2} (1 - e^{-f^2/\omega^2})$$

where $\omega$ determines the low-frequency cutoff, and $\sigma$ determines the high frequency cutoff, respectively.

The data may also be conditioned by background subtraction using a non-linear filter such as an erosion filter, with or without a low-pass filter to eliminate systemic noise. The preferred low-pass filtration technique is non-causal gaussian convolution.

Figure 4C:
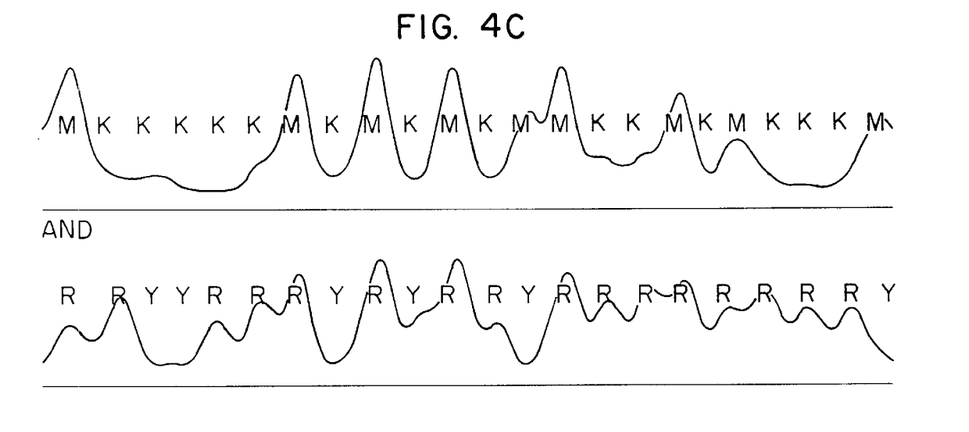

Next, in FIG. 4C, the data traces have been separated for clarity. Peaks and so-called "missing peaks" are identified according to methods disclosed in this application or in U.S. patent applications Ser. Nos. 08/497,202 and 08/670,534. In brief, two characteristics of each data trace are determined: the location of each peak and the number of missing peaks represented by each space between adjacent peaks.

Once both the number of missing bases and the peak data is obtained, the chromatographic output may be converted into a text file that states the sequential order of identified peaks and missing peaks. This text file is superimposed in FIG. 4C. These files can use standard or non-standard codes identifying bases. It should be noted that alignment of the peaks is rarely perfect if the two traces come from two different lanes of a gel, and that some allowances may need to be made for this imperfection in the interpretation of the text file. In general, a simple heuristic of half the peak spacing can be used to determine whether two bases are at the same position or not, i.e., if the peak positions differ by less than one-half of the peak spacing determined by the peak spacing function, the peaks are considered to be in the same position.

The bases at equivalent positions in the text files generated from the two reactions are compared, and the sequence of the nucleic acid is determined by the simple logical steps wherein (for the base experimental combinations used in this example):

|        | Lane 1   | peak | no peak |
|--------|----------|------|---------|
| Lane 2 |          |      |         |
| peak   |          | A    | G       |
| no peak|          | C    | T       |

Figure 4D:
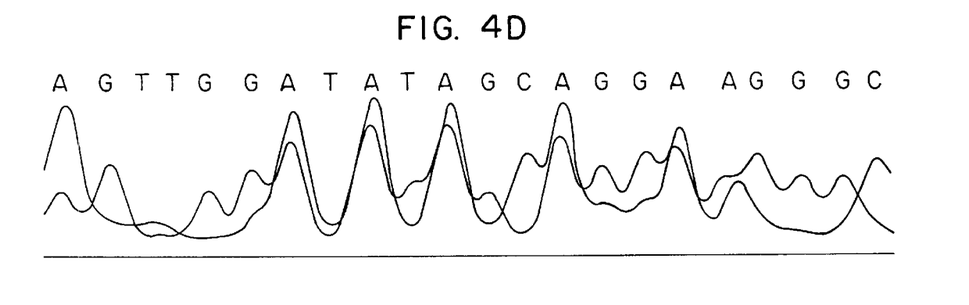

Similar logic tables can be set up and applied for other experimental base combinations. The results of the experiment in FIG. 4D reveal the sequence of the nucleic acid to be, in part, 5'-AGTTGGATATAGCAGGAAGGGC-3'    [Seq. ID No. 3]

which corresponds to a cryptic plasmid gene of *Chlamydia trachomatis*.

Another way to view the logical assignment of the bases based on the two data traces uses set theory. For example, if we assign M=AC, S=CG, K=GT=complement of M, W=AT, then the intersection of MS (i.e. intersection of AC and CG) is C, the intersection of MW is A, the intersection of KS is G, and the intersection of KW is T. The chromatograms shown in FIG. 4 can therefore be expressed as a text file of letters as follows:

first reaction: MMKMMMKKKMK . . . , (ie AC and not AC, for peaks and gaps, respectively)
second reaction: SWWSWSWSWSS . . . , (ie CG and not CG)
which yields the sequence
CATCACTGTCG . . .
when the two text files are combined according to the rules set forth above.

Figure 5A:
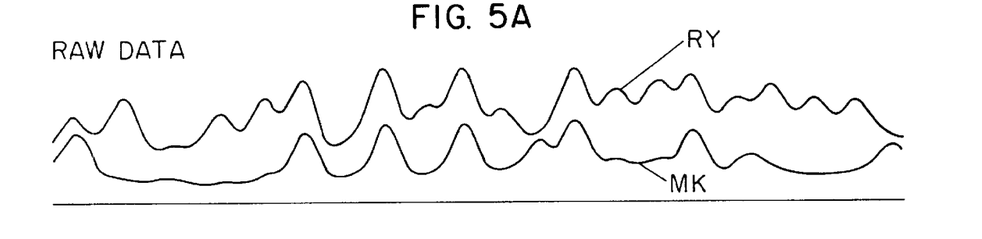
FIGS. 5A–5D show data manipulation of real data from sequencing of a target nucleic acid polymer using the method of the invention.
Figure 5B:
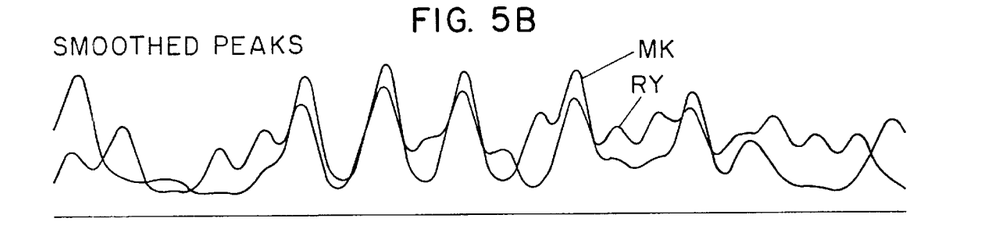
Figure 5C:
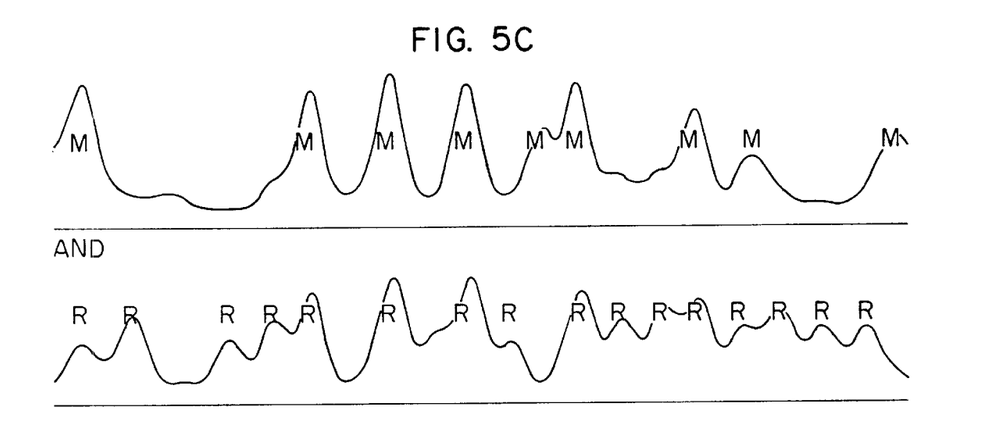

Another embodiment of the invention is preferred for use with OpenGene™ System DNA Sequencer (Visible Genetics Inc., Toronto). In this method, FIG. 5, the two termination reactions are electrophoresed in two contiguous lanes of a MicroCel electrophoresis gel cassette. This ensures a high degree of alignment of reaction products in each lane. The data traces are smoothed or conditioned (FIG. 5B). Peaks—but not "missing peaks"—are then identified in each chromatogram output as shown in FIG. 5C), and the position of each peak is recorded. The two lists of peaks and positions (one list from each data trace) are combined, and the software then looks for any blank positions in the combined list. Any blanks that are wide enough to span a "missing" a peak are identified. The number of peaks to be inserted into a blank can be determined using deconvolution techniques similar to those described previously. This method is superior because twice as many peaks are identified before deconvolution of the gaps. Since the accuracy of the deconvolution process depends on accurate determination of width of a singleton peak, overall accuracy is improved.

Figure 5D:
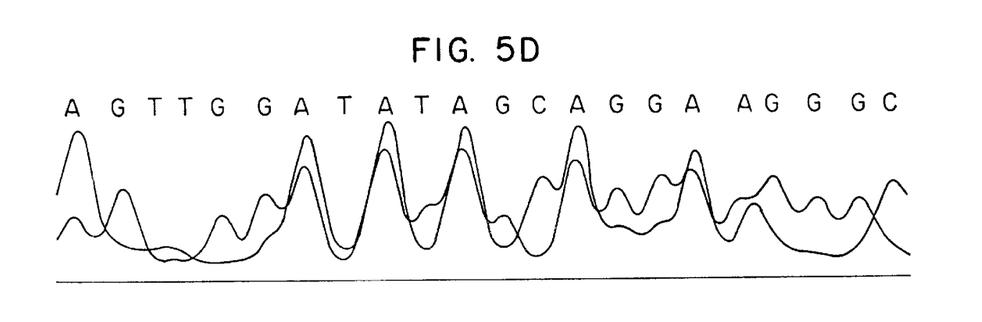

After the combined list is generated, including all missing peaks, the software then analyzes the combined list and designates the full 4 nucleotide sequence using the same logic applied in the previously discussed approaches. The results of this evaluation are shown in FIG. 5D.

The method of the invention can be used to determine the sequence of both homozygous and heterozygous samples and to mixed populations of similar nucleic acids, for example a mixed population of infectious microorganisms. Current chain termination technology using the enzyme Thermo Sequenase™ (Amersham Life Science) results in sequencing chromatograms wherein peaks have very consistent heights, in contrast to previously used enzymes. As a result, a heterozygote can now be routinely detected as half-height peak. This requires a simple modification to the peak detection software such that after a peak is detected, the peak's height or area or some other feature is measured to "quantify" the peak. A parameter is defined by the user which determines whether the peak quantity is full height or half-height. This parameter may in part be based on surrounding peak heights.

When the target DNA is heterozygous at a location the peaks displayed may be in the following combinations (again assuming that the terminators used are AC in the first reaction and AG in the second reaction):

|                              | Trace 1      | Trace 2      |
|------------------------------|--------------|--------------|
| bases in alleles of heterozygote |              |              |
| A/C                          | full height  | half height  |
| A/T                          | half height  | half height  |
| A/G                          | half height  | full height  |
| C/T                          | half height  | no peak      |
| C/G                          | half height  | half height  |
| G/T                          | no peak      | half height  |

As shown, the combined traces produce a unique result for all but two of heterozygote pairs (A/T and C/G) which produce a half height peak in each data trace. The this ambiguous result is obtained, the operator will need to flag the sequence and have the sample reanalyzed. However, where the number of potentially heterozygous alleles with clinical significance is small, it will generally be possible to select the three bases used so that diagnostically relevant data will normally be obtained at relevant sites.

When mixed populations of microorganisms are being analyzed, they may be present in widely varying amounts. Employing the method of the invention on a MicroGene Blaster automated DNA sequencer (Visible Genetics Inc.) allows detection of minority species present in quantities at least below 20% of the standard peak height.

The sequencing fragments formed in the method of the present invention are labeled with a detectable label. This label is preferably a fluorescent label suitable for use in a known automated DNA sequencer. Specific labels include fluorescein, cyanine dyes such as Cy5.0 and Cy5.5, and Texas Red. Labels may also be colored labels, chemiluminescent labels, chromogenic labels or any other label which can be detected at levels found in the gel electrophoresis of sequencing fragments.

The labels are preferably introduced into the sequencing fragments as part of the primer. However, detectable labels can be incorporated into the chain terminators where only one sequencing primer is provided. Use of labeled chain terminators with cycle sequencing or other processes where both DNA strands are copied would result in a confusing mixture of products that would be difficult if not impossible to analyze.

In each sequencing reaction, the fragments generated from one strand (either the sense or antisense strand) of the target DNA are labeled with a common label. Thus, for example, if a sequencing reaction is performed using both ddA and ddC chain terminators, the primer that hybridizes to the strand to be sequenced is suitably labeled with one type of detectable label such a fluorescein. In the second sequencing reaction, using for example ddA and ddT terminators, the same labeled primer can be employed. Alternatively, the primer in the second sequencing reaction can be the same primer, but labeled with a different detectable label. In this case, two optical systems may be required in an apparatus to provide excitation/detection of two distinct fluorophores. On the other hand, the product mixtures can be combined and run in a single gel, thus further increasing throughput.

When the sequencing fragments are generated in the two reactions using both forward and reverse primers, either or both of the primers may be labeled. If both primers are labeled, they must be labeled with distinguishable labels. Using two labels of this type in each reaction will permit determination of the sequences of both strands in two lanes (if the labels used in each reaction are the same) or a single lane (if the forward and reverse primers in each reaction are distinctly labeled, for example with the four dyes used as labels for the A, C, G and T reactions for analysis on an Applied Biosystems Inc. Prism 4-dye sequencer).

Figure 6:
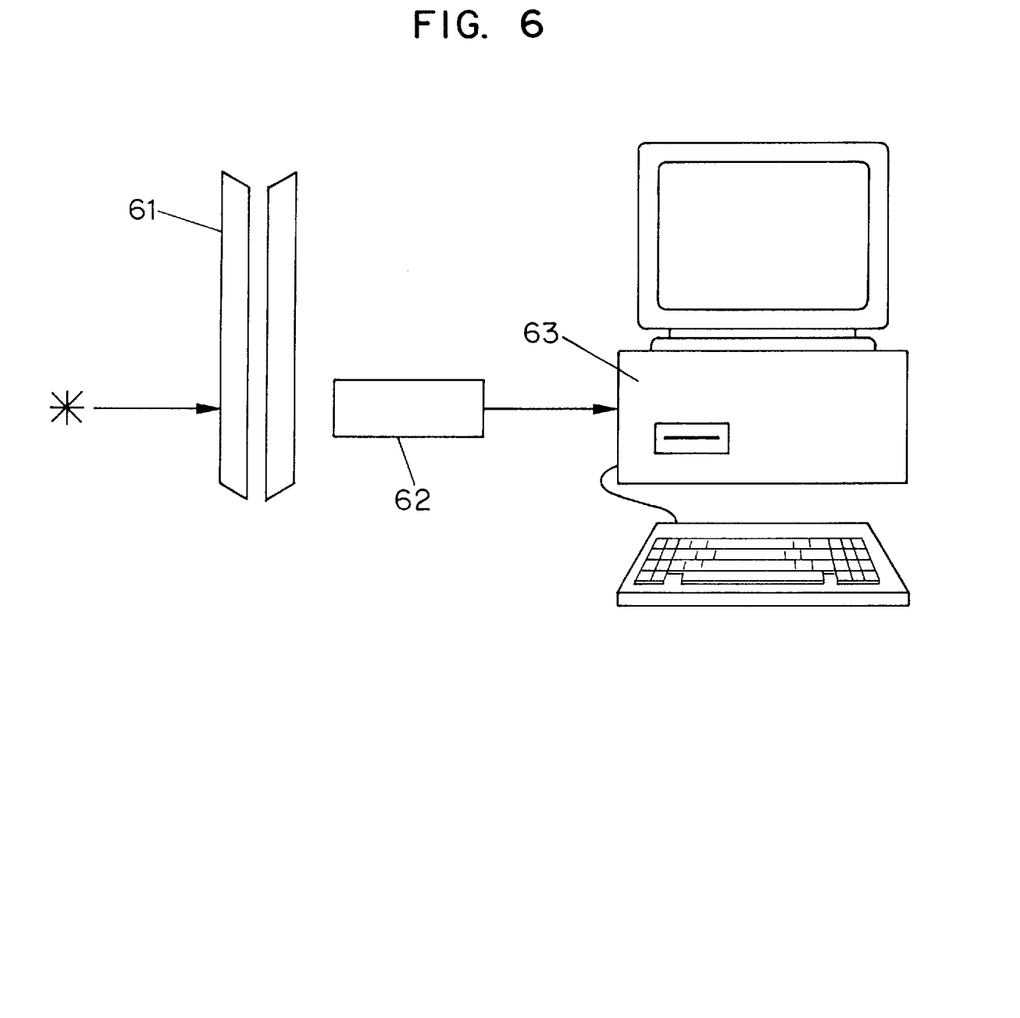
FIG. 6 shows an apparatus according to the invention schematically.

The method of the present invention is suitably practiced using an apparatus which is specifically adapted for the analysis of the two data traces produced. Such an apparatus can comprise an otherwise conventional DNA sequencer, such as an Pharmacia ALF or Visible Genetics MicroGene Blaster™, combined with a data processor which has a programmed instruction set which interprets the two data traces obtained using the method of the invention and outputs the resulting sequence. Thus, as illustrated diagrammatically in FIG. 6, an apparatus according to the invention comprises:

(a) means 61 for separating a mixture of chain termination sequencing fragments formed from the target DNA molecule based upon the length of the fragments;

(b) means 62 for detecting the separated chain termination sequencing fragments to produce an output signal; and (c) means 63 for analyzing the output signal to determine the sequence of the target DNA molecule, wherein the output signal produced consists of two data traces, one representing The lengths of chain termination sequencing fragments ending in either a first or a second chain terminator and the other representing the lengths of chain termination sequencing fragments ending in either the first or a third chain terminator, said first, second and third chain terminators each being analogs of a different nucleotide base.

Means 61 for separating a mixture of chain termination sequencing fragments formed from the target DNA molecule based upon the length of the fragments will generally by an electrophoresis apparatus in which a gel (e.g. a polyacrylamide gel) or other separation medium containing the sample to be analyzed is placed in an electric field to induce migration of the sample.

The specific nature of means 62 for detecting the separated chain termination sequencing fragments to produce an output signal will depend on the nature of the detectable labels being employed. For fluorescent, chemiluminescent, colored or chromogenic labels, this will include any necessary excitation source (e.g. a laser or light-emitting diode) combined with one or more detectors, e.g. photomultipliers, photodiodes and the like. Preferably, the detection system is disposed to collect real-time data from each of a plurality of lanes within the separation medium. A suitable combination of disclosed in commonly assigned U.S. patent application Ser. No. 08/353,932, U.S. Pat. No. 5,710,628, and PCT Application No. PCT/US95/15951, which are incorporated herein by reference.

Means 62 for detecting the separated chain termination sequencing fragments to produce an output signal are operatively connected to means 63 for analyzing the output signal to determine the sequence of the target DNA molecule. Means 63 may be a personal computer (for example with a PENTIUM or similar processor) or larger computer (e.g. a NextStep or RS6000 mini-computer) programmed with an appropriate instruction set to analyze an output signal consisting of two data traces, one representing the lengths of chain termination sequencing fragments ending in either a first or a second chain terminator and the other representing the lengths of chain termination sequencing fragments ending in either the first or a third chain terminator.

FIG. 7 shows a flow-chart of analysis steps to be accomplished by the programmed instruction set which is a part of means 63 for one embodiment of the invention. It will be appreciated, however, that the alignment step at the beginning of the flow chart is optional, depending on the quality of the starting data traces, and that other methods for identification of peaks and missing peaks may be employed. Thus, the basic steps which are performed by an apparatus according to the invention are (1) identification of peak and missing peak positions in the data traces; and (2) logical assignment of the base at each position in the target sequence based on the peak and missing peak positions.

EXAMPLE

The data traces of FIGS. 4A–D illustrate the use of the present invention to determine the sequence of a cryptic plasmid gene of *Chlamydia trachomatis*.

Two termination reactions were performed each using forward and reverse primers. A Pre-Reaction mixture was first generated as follows:

|  | Volume |
| --- | --- |
| Patient Sample DNA (prepared from urine sample ~ 300 ng) | 8.75 ul |
| Primer KL1-Cy5.5 labeled (10 uM) | 2.35 ul |
| Primer CT1590 (10 uM) | 1.58 ul |
| Enzyme Dilution Buffer (Stock; Amersham) | 6.3 ul |
| Thermo Sequenase Enzyme (32 U/ul Stock; Amersham) | 0.7 ul |
| Thermo Sequenase Reaction Buffer (pH 8.3; Mg 30 mM) | 7 ul |

| | Volume |
|---|---|
| ddH2O | 18.82 ul |
| Pre-Reaction Mixture Total Volume | 45.5 ul |

3 ul of the Pre-Reaction Mixture is combined with 3 ul of each Termination Mix, mixed well and treated to the following temperature cycles:

| 94° C. | 5 mins |
|---|---|
| then 40 cycles of | |
| 94° C. | 30 sec |
| 52° C. | 30 sec |
| 70° C. | 60 sec | and a final treatment of 70° C. for 60 sec. The reaction is stored on ice. 6 ul of Stop/Loading Buffer (100% formamide; colored dye) is added and mixed, and 1.5 ul is loaded into a single well of an electrophoresis gel in a MicroGene Blaster Automated DNA Sequencer (Visible Genetics Inc., Toronto, Canada). Each termination mix is loaded in a separate well.

The samples were electrophoresed and detected using a Visible Genetics MicroGene Blaster™ Automated DNA Sequencer to produce the two data traces shown in FIG. 4A. The analysis of these data traces is discussed above.

We claim:

1. A method for identifying the sequence of a target nucleic acid polymer comprising the steps of:
    (a) performing a first chain-extension sequencing reaction on the target nucleic acid polymer in a reaction mixture containing first and second chain-terminating nucleotides to produce a first product mixture containing commonly-labeled polynucleotide fragments complementary to a first strand of the target nucleic acid polymer, each fragment in the mixture starting at a location determined by a sequencing primer and being terminated with the first or second nucleotide;
    (b) performing a second chain extension sequencing reaction on the target nucleic acid polymer in a reaction mixture containing the first and a third chain-terminating fnucleotide to produce a second product mixture containing commonly-labeled polynucleotide fragments complementary to the first strand of the target nucleic acid polymer, each fragment in the mixture starting at the location determined by the sequencing primer and being terminated with the first or the third nucleotide, said first, second and third chain-terminating nucleotides each being different and selected from the group consisting of chain-terminating analogs of A, C, G and T; and
    (c) determining the sequence of the target nucleic acid polymer by evaluating a set of data traces consisting of first and second data traces reflecting the lengths of the polynucleotide fragments in the first and second product mixtures to determine the sequence of the target nucleic acid polymer.

2. The method of claim 1, wherein the polynucleotide fragments complementary to the first strand of the target nucleic acid polymer in the first product mixture are labeled with the same label as the polynucleotide fragments complementary to the first strand of the target nucleic acid polymer in the second product mixture.

3. The method of claim 1, wherein the polynucleotide fragments complementary to the first strand of the target nucleic acid polymer in the first product mixture are labeled with a label that is spectroscopically distinguishable from the label on the polynucleotide fragments complementary to the first strand of the target nucleic acid polymer in the second product mixture.

4. The method according to claim 1, wherein the first and second chain extension sequencing reactions generate reaction products complementary to both strands of the target nucleic acid using a forward and a reverse primer in each reaction.

5. The method according to claim 4, wherein one of the forward and reverse primers in each of the first and second reactions are labeled.

6. The method according to claim 5, wherein the labeled primer in the first reaction is labeled with the same label as the labeled primer in the second reaction.

7. The method according to claim 5, wherein the labeled primer in the first reaction is labeled with a label which is spectroscopically distinguishable from the label on the labeled primer in the second reaction.

8. The method according to claim 4, wherein both the forward and reverse primers in each of the first and second reactions are labeled, the label on the forward primer being spectroscopically distinguishable from the label on the reverse primer.

9. The method according to claim 8, wherein the forward primer in the first reaction is labeled with the same label as the forward primer in the second reaction, and the reverse primer in the first reaction is labeled with the same label as the reverse primer in the second reaction.

10. The method according to claim 8, wherein the forward primer in the first reaction is labeled with a label that is spectroscopically distinguishable from the label on the forward primer in the second reaction, and the reverse primer in the first reaction is labeled with a label that is spectroscopically distinguishable from the label on the reverse primer in the second reaction.

11. A method for identifying the sequence of a target nucleic acid polymer comprising the steps of:
    (a) performing a first chain-extension sequencing reaction on the target nucleic acid polymer in a reaction mixture containing first and second chain-terminating nucleotides to produce a first product mixture containing commonly-labeled polynucleotide fragments complementary to a first strand of the target nucleic acid polymer, each fragment in the mixture starting at a location determined by a sequencing primer and being terminated with the first or second nucleotide;

(b) performing a second chain extension sequencing reaction on the target nucleic acid polymer in a reaction mixture containing the first and a third chain-terminating nucleotide to produce a second product mixture containing commonly-labeled polynucleotide fragments complementary to the first strand of the target nucleic acid polymer, each fragment in the mixture starting at the location determined by the sequencing primer and being terminated with the first or the third nucleotide, said first, second and third chain-terminating nucleotides each being different and selected from the group consisting of chain-terminating analogs of A, C, G and T; and (c) evaluating the lengths of the polynucleotide fragments in the first and second product mixtures to determine the sequence of the target nucleic acid polymer, wherein the lengths of the polynucleotide fragments are evaluated by electrophoretically separating the first and second product mixtures and obtaining two aligned data traces; identifying peaks and missing peaks in the aligned data traces, and logically assigning bases in the sequence based on the identification of peaks and missing peaks.

12. A method for evaluating the sequence of a nucleic acid polymer comprising the steps of:

(a) obtaining a pair of aligned data traces, a first data trace representing the positions of a first and a second nucleotide within the nucleic acid polymer and a second data trace representing the positions of a the first and a third nucleotide within the nucleic acid polymer, said first, second and third nucleotides being different from one another;

(b) identifying peaks and assigning a number of missing peaks to each gap between peaks in the data traces; and (c) identifying the nucleotide present at each position in the nucleic acid polymer, wherein the presence of a peak at any given position in both data traces indicates the presence of the first nucleotide at that position, the presence of a peak at any given position in the first data trace but not the second data trace indicates the presence of the second nucleotide at that position, the presence of a peak at any given position in the second data trace but not the first data trace indicates the presence of the third nucleotide at that position, and the absence of a peak at any given position in either data trace indicates the presence of a fourth nucleotide, different from the first, second and third nucleotides, at that position.

13. An apparatus for determining the sequence of a target nucleic acid polymer, comprising:

(a) means for separating a mixture of chain termination sequencing fragments formed from the target nucleic acid polymer based upon the length of the fragments;

(b) means for detecting the separated chain termination sequencing fragments to produce an output signal;

(c) means for analyzing the output signal to determine the sequence of the target nucleic acid polymer, wherein the output signal produced consists of two data traces, one representing the lengths of chain termination sequencing fragments ending in either a first or a second chain terminator and the other representing the lengths of chain termination sequencing fragments ending in either the first or a third chain terminator, said first, second and third chain terminators each being analogs of a different nucleotide base.

14. The apparatus according to claim 13, wherein the means for analyzing the output signal is a computer programmed to identify peak and missing peak positions in the two data traces and to assign a base for each sequence position in the target nucleic acid polymer based on the peak and missing peak positions.

15. The apparatus according to claim 14, wherein the computer is further programmed to align the data traces prior to identifying the peak and missing peak positions.

16. The apparatus according to claim 15, wherein the computer is programmed to identify the peak and missing peak positions by performing the steps of performing an initial identification of peaks in each data trace based on height criteria;

selecting a subset of the identified peaks comprising the 40 to 50% of the peaks most likely to represent only one base;

generating standard height and width functions from the selected subset of peaks;

applying the standard height and width functions to the data traces to identify a refined set of singleton peaks;

determining a standard peak spacing function based on the spacing between peaks in the refined set of singleton peaks;

deconvolving non-singleton peaks into multiple peaks based on the peak spacing function; and assigning an integer number of missing peaks to each gap between peaks based on the peak spacing function.

17. The apparatus according to claim 14, wherein the computer is programmed to identify the peak and missing peak positions by performing the steps of performing an initial identification of peaks in each data trace based on height criteria;

selecting a subset of the identified peaks comprising the 40 to 50% of the peaks most likely to represent only one base;

generating standard height and width functions from the selected subset of peaks;

applying the standard height and width functions to the data traces to identify a refined set of singleton peaks;

determining a standard peak spacing function based on the spacing between peaks in the refined set of singleton peaks;

deconvolving non-singleton peaks into multiple peaks based on the peak spacing function; and assigning an integer number of missing peaks to each gap between peaks based on the peak spacing function.

18. The apparatus according to claim 13, wherein the two data traces are each aligned to standard data traces using text-based alignment and then combined to make a callable text file.

19. An apparatus for analyzing a data set consisting of two data traces from a nucleic acid sequencing reaction for a target nucleic acid polymer, one data trace representing the lengths of chain termination sequencing fragments ending in either a first or a second chain terminator and the other data trace representing the lengths of chain termination sequencing fragments ending in either the first or a third chain terminator, said first, second and third chain terminators each being analogs of a different nucleotide base, comprising means for analyzing the two data traces in the data set to determine the sequence of the target nucleic acid polymer.

20. The apparatus according to claim 19, wherein the means for analyzing the output signal is a computer programmed to identify peak and missing peak positions in the two data traces and to assign a base for each sequence position in the target nucleic acid polymer based on the peak and missing peak positions.

21. The apparatus according to claim 20, wherein the computer is further programmed to align the data traces prior to identifying the peak and missing peak positions.

22. The apparatus according to claim 21, wherein the computer is programmed to identify the peak and missing peak positions by performing the steps of performing an initial identification of peaks in each data trace based on height criteria;

selecting a subset of the identified peaks comprising the 40 to 50% of the peaks most likely to represent only one base;

generating standard height and width functions from the selected subset of peaks;

applying the standard height and width functions to the data traces to identify a refined set of singleton peaks;

determining a standard peak spacing function based on the spacing between peaks in the refined set of singleton peaks;

deconvolving non-singleton peaks into multiple peaks based on the peak spacing function; and assigning an integer number of missing peaks to each gap between peaks based on the peak spacing function.

23. The apparatus according to claim 20, wherein the computer is programmed to identify the peak and missing peak positions by performing the steps of performing an initial identification of peaks in each data trace based on height criteria;

selecting a subset of the identified peaks comprising the 40 to 50% of the peaks most likely to represent only one base;

generating standard height and width functions from the selected subset of peaks;

applying the standard height and width functions to the data traces to identify a refined set of singleton peaks;

determining a standard peak spacing function based on the spacing between peaks in the refined set of singleton peaks;

deconvolving non-singleton peaks into multiple peaks based on the peak spacing function; and assigning an integer number of missing peaks to each gap between peaks based on the peak spacing function.

24. The apparatus according to claim 19, wherein the means for analyzing the two data traces aligns the data traces to standard data traces using text-based alignment and then combines the aligned data traces to make a callable text file.

25. A method for identifying the sequence of a target nucleic acid polymer comprising the steps of:

(a) performing a first chain-extension sequencing reaction on the target nucleic acid polymer in a reaction mixture containing first and second chain-terminating nucleotides to produce a first product mixture containing commonly-labeled polynucleotide fragments complementary to a first strand of the target nucleic acid polymer, each fragment in the mixture starting at a location determined by a sequencing primer and being terminated with the first or second nucleotide;

(b) performing a second chain extension sequencing reaction on the target nucleic acid polymer in a reaction mixture containing the first and a third chain-terminating nucleotide to produce a second product mixture containing commonly-labeled polynucleotide fragments complementary to the first strand of the target nucleic acid polymer, each fragment in the mixture starting at the location determined by the sequencing primer and being terminated with the first or the third nucleotide, said first, second and third chain-terminating nucleotides each being different and selected from the group consisting of chain-terminating analogs of A, C, G and T; and (c) obtaining a data set consisting of two data streams from evaluating the lengths of the polynucleotide fragments in the first and second product mixtures and processing the data set to determine the sequence of the target nucleic acid polymer.

\* \* \* \* \*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 20
      (B) TYPE: nucleic acid
      (C) STRANDEDNESS: double
      (D) TOPOLOGY: linear    (ii) MOLECULE TYPE: other nucleic acid    (iii) HYPOTHETICAL: no    (iv) ANTI-SENSE: yes    (v) FRAGMENT TYPE: internal    (vi) ORIGINAL SOURCE:
      (A) ORGANISM: Chlamydia trachomatis    (ix) FEATURE:
      (D) OTHER INFORMATION: sequencing primer    (xi) SEQUENCE DESCRIPTION: SEQ ID NO:1:

TCCGGAGCGA GTTACGAAGA                                                    20

(2) INFORMATION FOR SEQ ID NO: 2:

(i) SEQUENCE CHARACTERISTICS:
      (A) LENGTH: 20
      (B) TYPE: nucleic acid
      (C) STRANDEDNESS: double
      (D) TOPOLOGY: linear    (ii) MOLECULE TYPE: other nucleic acid    (iii) HYPOTHETICAL: no    (iv) ANTI-SENSE: no    (v) FRAGMENT TYPE: internal    (vi) ORIGINAL SOURCE:
      (A) ORGANISM: Chlamydia trachomatis    (ix) FEATURE:
      (D) OTHER INFORMATION: sequencing primer    (xi) SEQUENCE DESCRIPTION: SEQ ID NO:2:

```
ATGCCCGGGA TTGGTTGATC                                                          20

(2) INFORMATION FOR SEQ ID NO: 3:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: Chlamydia trachomatis (xi) SEQUENCE DESCRIPTION: SEQ ID NO:3:

AGTTGGATAT AGCAGGAAGG GC                                                       22
```